(12) United States Patent
Schwarz et al.

(10) Patent No.: US 10,500,330 B2
(45) Date of Patent: Dec. 10, 2019

(54) SYSTEM AND METHOD FOR WASHING SHED BLOOD

(71) Applicant: Haemonetics Corporation, Braintree, MA (US)

(72) Inventors: Donald J. Schwarz, South Easton, MA (US); Seth Kasper, Cambridge, MA (US); Lisa Fahey, Foxboro, MA (US)

(73) Assignee: Haemonetics Corporation, Braintree, MA (US)

( * ) Notice: Subject to any disclaimer, the term of this patent is extended or adjusted under 35 U.S.C. 154(b) by 266 days.

(21) Appl. No.: 15/517,351

(22) PCT Filed: Oct. 7, 2015

(86) PCT No.: PCT/US2015/054487
§ 371 (c)(1),
(2) Date: Apr. 6, 2017

(87) PCT Pub. No.: WO2016/057664
PCT Pub. Date: Apr. 14, 2016

(65) Prior Publication Data
US 2017/0246376 A1    Aug. 31, 2017

Related U.S. Application Data (60) Provisional application No. 62/060,886, filed on Oct. 7, 2014.

(51) Int. Cl.
*A61M 1/36* (2006.01)
*A61M 1/38* (2006.01)
(Continued)

(52) U.S. Cl.
CPC .......... *A61M 1/3692* (2014.02); *A61M 1/008* (2013.01); *A61M 1/3627* (2013.01);
(Continued)

(58) Field of Classification Search
CPC .. A61M 1/3692; A61M 1/008; A61M 1/3627; A61M 1/3672; A61M 1/38;
(Continued)

(56) References Cited

U.S. PATENT DOCUMENTS 3,645,252 A    2/1972 Gilford
3,655,123 A    4/1972 Judson et al.
(Continued)

FOREIGN PATENT DOCUMENTS

EP    0223126 A2    5/1987
EP    0573117 A1    12/1993
(Continued)

OTHER PUBLICATIONS

Ferraris et al., Perioperative blood transfusion and blood conservation in cardiac surgery: the Society of Thoracic Surgeons and the Society of Cardiovascular Anesthesiologists clinical practice guideline. Ann Thorac Surg. May 2007;83(5 Suppl):S27-86.
(Continued)

*Primary Examiner* — Philip R Wiest
(74) *Attorney, Agent, or Firm* — McCarter & English, LLP; Jonathan C. Lovely (57) ABSTRACT

A method for collecting and washing shed blood includes providing a blood salvage reservoir and a blood salvage system. The user may connect a vacuum inlet port on the reservoir to a vacuum outlet port on the salvage system, connect an inlet port on the reservoir to a patient, and connect a vacuum source to a vacuum connection port on the salvage system. The method may then (1) draw a vacuum on the reservoir to draw shed blood into the reservoir, (2) disconnect the reservoir from the surgical field and salvage system, and (3) connect a second reservoir. The first blood salvage reservoir may then be connected to an automated blood processing system, and the collected blood may be
(Continued)

introducing into the automated blood processing system and washed. The blood processing system may then return a portion of the washed blood to the patient.

23 Claims, 6 Drawing Sheets

(51) Int. Cl.
*A61M 1/00* (2006.01)
*A61M 27/00* (2006.01)

(52) U.S. Cl.
CPC ............ *A61M 1/3672* (2013.01); *A61M 1/38* (2013.01); *A61M 27/00* (2013.01); *A61M 2202/0429* (2013.01); *A61M 2205/3334* (2013.01); *A61M 2205/3379* (2013.01); *A61M 2209/082* (2013.01); *A61M 2209/084* (2013.01)

(58) Field of Classification Search
CPC .......... A61M 27/00; A61M 2202/0429; A61M 2205/3334; A61M 2205/3379; A61M 2208/082; A61M 2208/084
See application file for complete search history.

(56) References Cited

U.S. PATENT DOCUMENTS

| | | |
|---|---|---|
| 3,768,653 A | 10/1973 | Brumfield |
| 3,965,896 A | 6/1976 | Swank |
| 4,033,345 A | 7/1977 | Sorenson et al. |
| 4,054,523 A | 10/1977 | Ingenito et al. |
| 4,086,924 A | 5/1978 | Latham, Jr. |
| 4,115,277 A | 9/1978 | Swank |
| 4,189,470 A | 2/1980 | Rose |
| 4,236,960 A | 12/1980 | Hultman et al. |
| 4,243,531 A | 1/1981 | Crockett et al. |
| 4,321,192 A | 3/1982 | Jain |
| 4,411,786 A | 10/1983 | Russell |
| 4,416,654 A | 11/1983 | Schoendorfer et al. |
| 4,531,954 A | 7/1985 | Klein |
| 4,561,868 A | 12/1985 | von Reis et al. |
| 4,668,214 A | 5/1987 | Reeder |
| 4,673,423 A | 6/1987 | Yumlu |
| 4,680,025 A | 7/1987 | Kruger et al. |
| 4,681,677 A | 7/1987 | Kuh et al. |
| 4,704,203 A | 11/1987 | Reed |
| 4,743,371 A | 5/1988 | Servas et al. |
| 4,758,337 A | 7/1988 | Kohn et al. |
| 4,781,707 A | 11/1988 | Boehringer et al. |
| 4,795,448 A | 1/1989 | Stacey et al. |
| 4,828,543 A | 5/1989 | Weiss et al. |
| 4,872,988 A | 10/1989 | Culkin |
| 4,886,487 A | 12/1989 | Solem et al. |
| 4,898,572 A | 2/1990 | Surugue nee Lasnier et al. |
| 4,946,434 A | 8/1990 | Plaisted et al. |
| 4,954,251 A | 9/1990 | Barnes et al. |
| 5,015,388 A | 5/1991 | Pusineri et al. |
| 5,055,198 A * | 10/1991 | Shettigar ................. A61M 1/02 210/104 |
| 5,133,703 A | 7/1992 | Boehringer et al. |
| 5,135,645 A | 8/1992 | Sklenak et al. |
| 5,147,290 A | 9/1992 | Jonsson |
| 5,182,019 A | 1/1993 | Cote et al. |
| 5,183,569 A | 2/1993 | Kyriacou |
| 5,215,519 A | 6/1993 | Shettigar |
| 5,223,154 A | 6/1993 | MacPherson, Jr. et al. |
| 5,234,403 A | 8/1993 | Yoda et al. |
| 5,238,655 A | 8/1993 | Laible et al. |
| 5,294,401 A | 3/1994 | Hagiwara |
| 5,298,016 A | 3/1994 | Gordon |
| 5,311,908 A | 5/1994 | Barone et al. |
| 5,378,227 A | 1/1995 | O'Riordan et al. |
| 5,386,734 A | 2/1995 | Pusinelli |
| 5,411,472 A | 5/1995 | Steg, Jr. et al. |
| 5,411,705 A | 5/1995 | Thor et al. |
| 5,417,650 A | 5/1995 | Gordon |
| 5,419,759 A | 5/1995 | Naficy |
| 5,423,738 A | 6/1995 | Robinson et al. |
| 5,458,566 A * | 10/1995 | Herrig ................. A61M 1/3624 128/DIG. 13 |
| 5,464,399 A | 11/1995 | Boettger |
| 5,554,293 A | 9/1996 | Uhoch |
| 5,634,893 A | 6/1997 | Rishton |
| 5,643,193 A * | 7/1997 | Papillon ............... A61M 1/3621 604/6.07 |
| 5,651,766 A | 7/1997 | Kingsley et al. |
| 5,658,256 A | 8/1997 | Shields |
| 5,674,173 A | 10/1997 | Hlavinka et al. |
| 5,725,777 A | 3/1998 | Taylor |
| 5,733,253 A | 3/1998 | Headley et al. |
| 5,770,073 A | 6/1998 | Bach et al. |
| 5,800,721 A | 9/1998 | McBride |
| 5,879,624 A | 3/1999 | Boehringer et al. |
| 5,891,080 A | 4/1999 | Skinkle et al. |
| 5,954,971 A | 9/1999 | Pages et al. |
| 5,971,948 A | 10/1999 | Pages et al. |
| 6,007,472 A | 12/1999 | Schill et al. |
| 6,250,330 B1 | 6/2001 | Welker |
| 6,251,284 B1 | 6/2001 | Bischof et al. |
| 6,251,291 B1 | 6/2001 | Lamphere et al. |
| 6,464,624 B2 | 10/2002 | Pages |
| 6,508,778 B1 | 1/2003 | Verkaart et al. |
| 6,632,189 B1 | 10/2003 | Fallen et al. |
| 6,632,191 B1 | 10/2003 | Headley et al. |
| 6,723,086 B2 | 4/2004 | Bassuk et al. |
| 6,800,072 B2 | 10/2004 | Patzer |
| 6,890,316 B2 | 5/2005 | Rawles et al. |
| 8,157,103 B2 | 4/2012 | Eagle et al. |
| 8,409,125 B2 | 4/2013 | Bobroff |
| 8,628,671 B2 | 1/2014 | Eagle et al. |
| 2005/0203469 A1 | 9/2005 | Bobroff et al. |
| 2008/0058695 A1* | 3/2008 | Perovitch ............ A61M 1/0001 604/6.03 |
| 2013/0197470 A1* | 8/2013 | Bobroff ............... A61M 1/0209 604/500 |

FOREIGN PATENT DOCUMENTS

| | | |
|---|---|---|
| EP | 0682953 A1 | 11/1995 |
| EP | 0771570 A1 | 5/1997 |
| EP | 1166806 A2 | 1/2002 |
| JP | H04236960 A | 8/1992 |
| JP | H11-506030 A | 6/1999 |
| JP | 2008-538514 A | 10/2008 |
| WO | 1984/00892 A1 | 3/1984 |
| WO | 1989/01792 A1 | 3/1989 |
| WO | 1989/04709 A1 | 6/1989 |
| WO | 1994/21311 A2 | 9/1994 |
| WO | 1995/03840 A1 | 2/1995 |
| WO | 1996/40319 A1 | 12/1996 |
| WO | 1998/14163 A1 | 4/1998 |
| WO | 2000/38756 A1 | 7/2000 |
| WO | 2006/100651 A1 | 9/2006 |

OTHER PUBLICATIONS

International Search Report and Written Opinion for Application No. PCT/US2015/054487, dated Jan. 6, 2016, 11 pages.
Supplementary European Search Report for Application No. 15848979.9, dated Apr. 18, 2018, 12 pages.

* cited by examiner

SYSTEM AND METHOD FOR WASHING SHED BLOOD

This patent application claims priority from U.S. Provisional Patent Application Ser. No. 62/060,886, filed Oct. 7, 2014, entitled, "SYSTEM AND METHOD FOR WASHING SHED BLOOD," and naming Donald Schwarz, Seth Kasper, and Lisa Fahey as inventors, the disclosure of which is incorporated herein, in its entirety, by reference.

TECHNICAL FIELD

The present invention relates to the collection of shed blood, and more particularly to systems and methods for washing shed blood.

BACKGROUND ART

In many applications it is desirable to drain and collect blood and other fluids from wounds and surgical sites (e.g., intra-operatively and/or post-operatively). Not only does the removal of fluids aid in healing and reduce the threat of infection, when blood is collected, it provides the hospital the opportunity to return the collected blood back to the patient. This, in turn, reduces the need to transfuse blood that is not the patient's own blood (e.g., allogeneic blood).

Prior-art systems for salvaging blood from surgical sites and wound drains often employ disposable units that include a reservoir for collecting the blood. The collected blood may then be re-infused into the patient. However, in many instances, the collected blood is not washed prior to being re-infused into the patient. Rather, the prior art systems merely pass the collected blood through a micro-aggregate blood filter to remove aggregates from the blood.

SUMMARY OF THE EMBODIMENTS

In a first embodiment of the invention there is provided a method for collecting and washing shed blood. The method includes providing a first blood salvage reservoir and a blood salvage system. The first blood salvage reservoir (e.g., a flexible reservoir) may include an inlet port, an outlet port and a vacuum inlet port. The blood salvage system may have a rigid housing, a vacuum connection port and a vacuum outlet port. The vacuum inlet port on the first blood salvage reservoir may be fluidly connected to the vacuum outlet port on the blood salvage system. The first blood salvage reservoir may be contained within a rigid frame that supports the first blood salvage reservoir.

The method may also include fluidly connecting the inlet port of the first blood salvage reservoir to a surgical field of a patient (e.g., via a chest drain and/or patient line), and fluidly connecting the vacuum connection port on the blood salvage system to a vacuum source. The inlet port may be configured to allow blood lost during a surgical procedure to be collected within the first blood salvage reservoir. The method may then (1) draw a vacuum on the first blood salvage reservoir and the blood salvage system to draw blood from the surgical field and into the blood salvage reservoir, and (2) collect a volume of shed blood within the first blood salvage reservoir.

Once the shed blood is collected, the method may disconnect the first blood salvage reservoir from the surgical field and the blood salvage system, and fluidly connect a second blood salvage reservoir to the surgical field and blood salvage system to continue drawing blood from the surgical field. The method may then fluidly connect the outlet port of the first blood salvage reservoir to an automated blood processing system, introduce the collected blood into the automated blood processing system, wash (using the automated blood processing system) the blood introduced into the automated blood processing system, and return (e.g., autologously) at least a portion of the washed blood to the patient.

In some embodiments, washing the blood introduced into the automated blood processing system may include (1) introducing anticoagulant into the collected blood, and (2) introducing the anticoagulated blood into a blood component separation device. The blood component separation device may separate the anticoagulated blood into red blood cells and at least a second blood component. The method may then send the second blood component to a waste container, and introduce a wash solution into the blood component separation device to wash the red blood cells. The method/system may return the washed red blood cells to the patient.

In additional embodiments, the method may include monitoring the amount of blood collected within the first blood salvage reservoir, and disconnecting the first blood salvage reservoir when a predetermined volume of blood is collected within the first blood salvage reservoir. The predetermined volume blood may be between 100 mL and 500 mL.

In further embodiments, the surgical site may be an intra-operative surgical site, and connecting the first blood salvage reservoir to the surgical site may include connecting the first blood salvage reservoir to an aspiration and anti-coagulant line. The outlet port of the first blood salvage reservoir may be fluidly connected to the automated blood processing system via a fluid connection set. The fluid connection set may include a first connector, a second connector, and a tube. The first connector (e.g., a spike) may connect to the outlet port of the first blood salvage reservoir, the second connector may connect to an inlet on the automated blood processing system, and the tube may extend between the first and second connector to fluidly connect the first blood salvage reservoir and the automated blood processing system. The fluid connection set may also include at least one valve that is located on the tube and configured to prevent the flow of fluid through the tube.

In some embodiments, disconnecting the first blood salvage reservoir from the surgical field and from the blood salvage system may include (1) fluidly disconnecting the inlet port on the first blood salvage reservoir from the surgical field, and (2) fluidly disconnecting the vacuum inlet port on the first blood salvage reservoir from the vacuum outlet port on the blood salvage system. Additionally or alternatively, fluidly connecting the second blood salvage reservoir to the surgical field and the blood salvage system may include (1) fluidly connecting a vacuum inlet port on the second blood salvage reservoir to the vacuum outlet port on the blood salvage system, and (2) fluidly connecting an inlet port on the second blood salvage reservoir to the surgical field of the patient.

In accordance with further embodiments, a method for collecting and washing shed blood may include providing a first blood salvage reservoir having an inlet port, an outlet port and a vacuum inlet port, and providing a blood salvage system having a vacuum connection port and a vacuum outlet port. The method may also include (1) fluidly connecting the vacuum inlet port on the first blood salvage reservoir to the vacuum outlet port on the blood salvage system, (2) fluidly connecting the inlet port of the first blood salvage reservoir to a surgical field of a patient, and (3)

fluidly connecting the vacuum connection port on the blood salvage system to a vacuum source. The inlet port may be configured to allow blood lost during a surgical procedure to be collected within the first blood salvage reservoir.

The method may then draw a vacuum on the first blood salvage reservoir and the blood salvage system to draw blood from the surgical field and into the blood salvage reservoir, and collect a volume of shed blood within the first blood salvage reservoir. Once the shed blood is collected, the method may disconnect the first blood salvage reservoir from the surgical field and from the blood salvage system, and fluidly connect a second blood salvage reservoir to the surgical field and blood salvage system to continue drawing blood from the surgical field.

To process the blood collected within the first blood salvage reservoir, the method may fluidly connect the outlet port of the first blood salvage reservoir to an automated blood processing system. The method may then introduce the collected blood into the automated blood processing system, wash the blood, and return at least a portion of the washed blood to the patient.

In accordance with additional embodiments, a method of blood salvage collection, processing and autologous reinfusion includes providing a first blood salvage reservoir and providing a rigid reservoir. The first blood salvage reservoir may include an inlet port and at least one outlet port. The rigid reservoir may have an inlet and outlet. The method may also include connecting the inlet port to the surgical field of a patient to collect blood lost during a surgical procedure, connecting the inlet of the rigid reservoir to the outlet of the blood salvage reservoir, and connecting the outlet of the rigid reservoir to a source of suction. The method may then operate the source of suction to draw blood from the surgical field into the blood salvage reservoir After collecting the blood, the method may (1) disconnect the blood salvage reservoir from the surgical field and from the rigid reservoir, and (2) connect a second blood salvage device to the surgical field and rigid reservoir to continue suctioning blood from the surgical field. The method may then connect an outlet of the first blood salvage reservoir to a fluid pathway inlet of an automated blood processing system, and operate the automated blood processing system to clean the salvaged blood and return it autologously to the patient.

In accordance with still further embodiments, a system for collecting and washing shed blood may include a first blood salvage reservoir for collecting shed blood, a blood salvage system, and a connection set. The first blood salvage reservoir may include (1) a flexible housing defining the first blood salvage reservoir, (2) an inlet port configured to be fluidly connected to a surgical field of a patient such that shed blood may be collected within the flexible housing, (3) a vacuum inlet port configured to allow a vacuum to be drawn on the first blood salvage reservoir to draw fluid from the surgical site and into the first blood salvage reservoir, and (4) an outlet located on a bottom surface of the flexible housing.

The blood salvage system may include a rigid housing defining the blood salvage system, a vacuum connection port configured to be fluidly connected to a vacuum source, and a vacuum outlet port configured to be fluidly connected the vacuum inlet port on the first blood salvage reservoir (e.g., to allow a vacuum to be drawn on the first blood salvage reservoir). The fluid connection set may include a first and second connector and a tube. The first connector may be configured to connect to the outlet port on the first blood salvage reservoir. The second connector may be configured to connect to an inlet on an automated blood processing system. The tube may extend between the first and second connectors, and the fluid connection set may fluidly connect the outlet of the first blood salvage reservoir and the automated blood processing system.

The first blood salvage reservoir may have a collection mode and a processing mode. When in the collection mode, the inlet port may be fluidly connected to the surgical site, the vacuum inlet port may be fluidly connected to the vacuum outlet port on the blood salvage system, and the first blood salvage reservoir may collect shed blood from the surgical site. When in the processing mode, the inlet port may be fluidly disconnected from the surgical site, the vacuum inlet port may be fluidly disconnected from the vacuum outlet port on the blood salvage system, and the first connector on the fluid connection set may be connected to the outlet to fluidly connect the first blood salvage reservoir to the automated blood processing system. The automated blood processing system may process and autologously reinfuse at least a portion of the shed blood.

In some embodiments, the system may also include a second blood salvage reservoir for collecting shed blood. The second blood salvage reservoir may include a second flexible housing defining the second blood salvage reservoir, a second inlet port, and a second vacuum inlet port. The second inlet port may be fluidly connected to the surgical field when the first blood salvage reservoir is in the processing mode, such that shed blood may be collected within the second flexible housing. The second vacuum inlet port may be configured to allow a vacuum to be drawn on the second blood salvage reservoir to draw fluid from the surgical site and into the second blood salvage reservoir when the first blood salvage reservoir is in the processing mode.

BRIEF DESCRIPTION OF THE DRAWINGS

The foregoing features of embodiments will be more readily understood by reference to the following detailed description, taken with reference to the accompanying drawings, in which.

DETAILED DESCRIPTION OF SPECIFIC EMBODIMENTS

In illustrative embodiments, a system for collecting and washing shed blood may have a blood salvage reservoir and a blood salvage system. The blood salvage reservoir may include a vacuum inlet port that is connected to a vacuum outlet port on the salvage system, and an inlet (e.g., a fluid/blood inlet) that is fluidly connected to a surgical field so that shed blood may be collected in the reservoir. The reservoir may be disconnected from the salvage system and connected to a blood processing system so that the collected shed blood can be washed and a portion of the washed blood (e.g., the red blood cells) may be returned to the patient.

Figure 1:
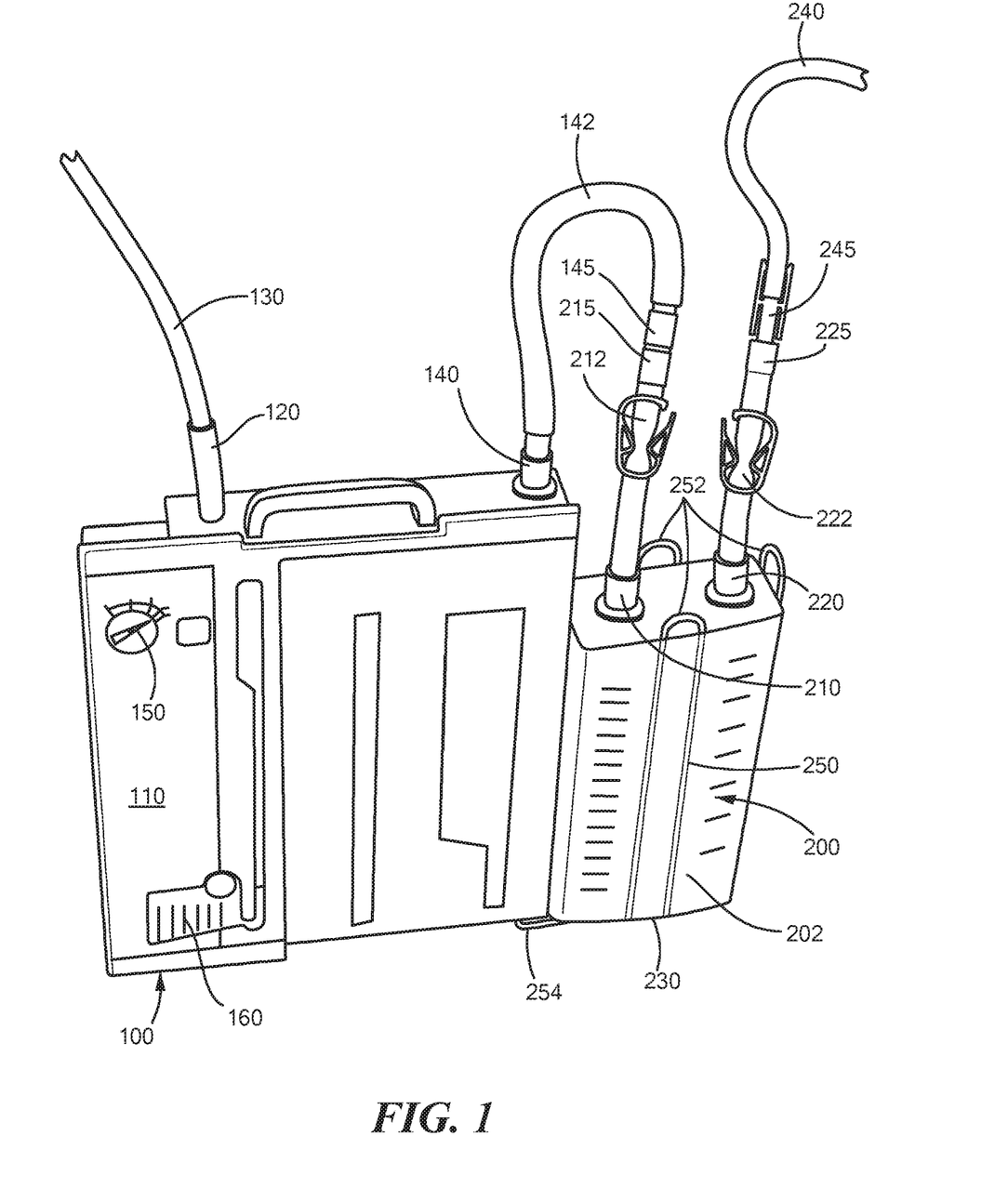
FIG. 1 schematically shows a system for collecting shed blood, in accordance with various embodiments of the present invention.

FIG. 1 shows a blood salvage system 100 and blood salvage reservoir 200 in accordance with some embodiments of the present invention. The blood salvage system 100 includes a housing 110 having an interior volume (e.g., having one or more cavities/reservoirs) in which fluids may be collected, and a number of ports located on the top of the housing 110. For example, the blood salvage system 100 may include a vacuum connection port 120 that, as discussed in greater detail below, can be connected to a vacuum source (not shown) via a tube 130. Additionally, the blood salvage system 100 can also include a vacuum outlet port 140. As also discussed in greater detail below, the vacuum outlet port 140 may be connected to the blood salvage reservoir 200 to draw a vacuum on the reservoir 200.

To ensure that the blood salvage system 100 doesn't collapse under vacuum, the housing 110 can be rigid. In some embodiments, the blood salvage system 100 can include a number of other components and features to help control the amount of vacuum and protect the patient. For example, the blood salvage system 100 can include a suction control regulator 150 that controls the level of suction within the surgical site, and a water seal 160 to help prevent air from re-entering the patient's surgical site. An exemplary blood salvage system 100 is produced by Teleflex Incorporated—in particular, the Teleflex Pluer-Evac® A-9250-08LF.

Figure 4:
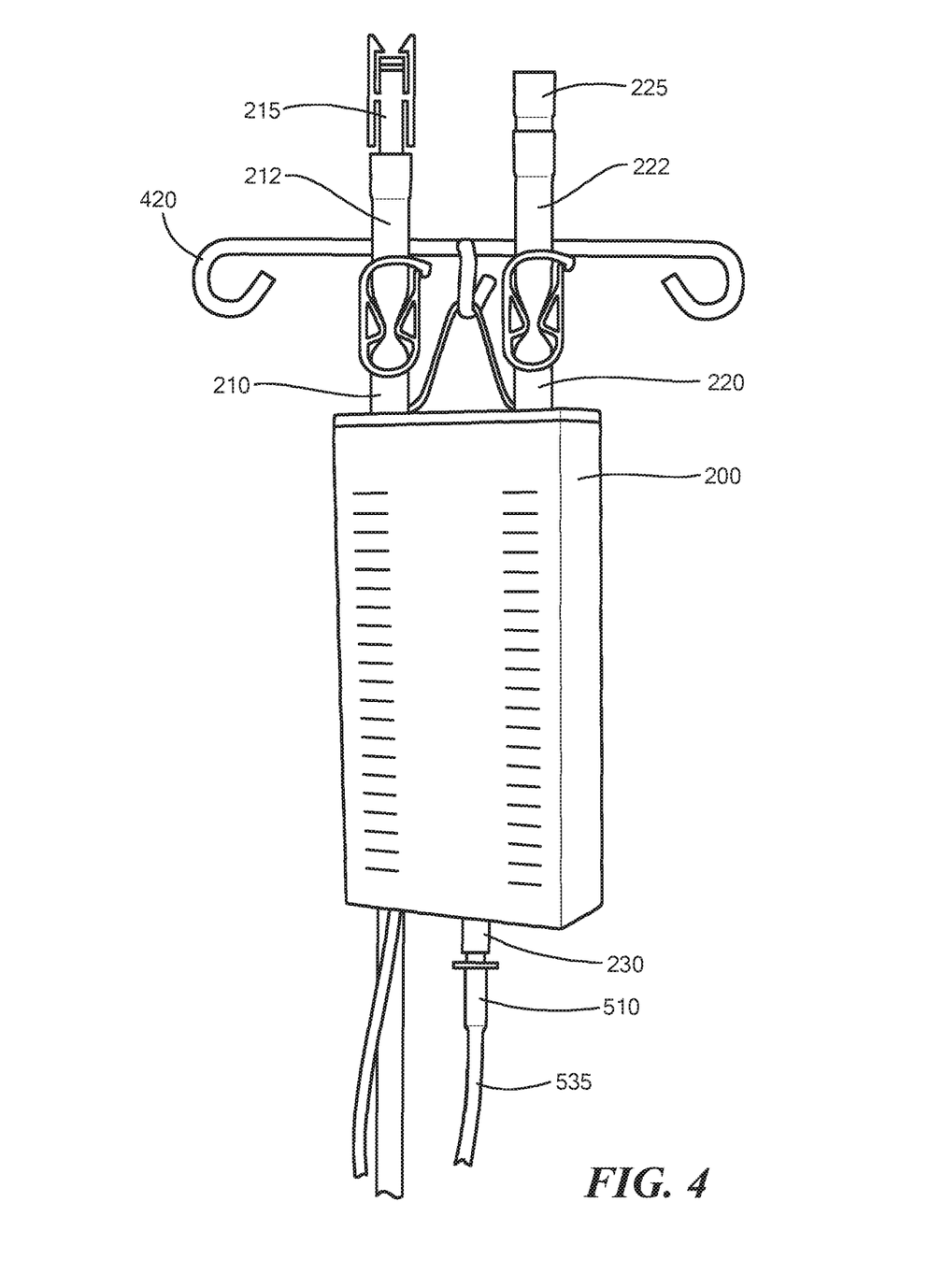
FIG. 4 schematically shows a closer view of the blood salvage reservoir shown in FIG. 3, in accordance with some embodiments of the present invention.

As shown in FIGS. 1 and 4, the blood salvage reservoir 200 may be a soft walled reservoir and, like the blood salvage system 100, have a number of ports for connecting the reservoir 200 to the blood salvage system 100 and the patient (e.g., to the surgical site). For example, the reservoir 200 may have a vacuum inlet port 210 that fluidly connects to the vacuum outlet port 140 on the blood salvage system 100 (e.g., so that the blood salvage system 100 can pull a vacuum on the reservoir 200). Additionally, the reservoir 200 may include an inlet port 220 that fluidly connects to the surgical site of the patient. An exemplary blood salvage reservoir 200 is produced by Teleflex Incorporated—in particular, the Teleflex Pluer-Evac® A-1500-08LF autotransfusion bag.

To help facilitate the fluid connections between the various components (e.g., the blood salvage system 100, the reservoir 200, and the vacuum source) and the patient, some embodiments may have connectors (e.g., quick connect/disconnect connectors) between the various ports (and/or tubing leading from the ports). For example, the vacuum outlet port 140 (or a section of tubing 142 leading from the vacuum outlet port 140) can include a connector 145 that can be connected to and disconnected from a connector 215 on the vacuum inlet port 210 on the reservoir 200 (or a tube 212 leading from the vacuum inlet port 210). Similarly, the inlet port 220 on the reservoir 200 (or a tube 222 leading from the inlet port 220) can include a connector 225 that can be connected to and disconnected from a connector 245 located on a tube leading to the patient (e.g., the patient tube 240). In this manner, the various components and tubes of the system can be connected and disconnected as needed.

In addition to the vacuum inlet port 210 and the fluid inlet port 220, some embodiments of the blood salvage reservoir 200 may also include an outlet port 230 (e.g., a spike port) located on the bottom of the reservoir 200. As discussed in greater detail below, once shed blood is collected within the reservoir 200, the outlet port 230 may be used to transfer the shed blood collected within the reservoir 200 to a blood processing system 400 (FIG. 3) for processing, washing, and return to the patient.

As mentioned above, the blood salvage reservoir 200 can be flexible (e.g., it can have soft/flexible walls). To prevent the reservoir 200 from collapsing under the vacuum supplied by the blood salvage system 100 and ease fluid collection, the reservoir 200 may include a removable rigid frame 250 that generally maintains the shape of the reservoir 200 during collection. For example, the frame 250 may include one or more extensions 252 (e.g., one on each side of the frame 250) that extend upwards from the base 252 of the frame 250. In such embodiments, the reservoir 200 may be slid over/onto the frame 250 such that the extensions pass through pockets/sleeves 202 located on each side of the reservoir 200. Also, the rigid frame 250 may connect to the blood salvage system 100 to secure the reservoir 200 to the blood salvage system 100. Alternatively, to prevent the reservoir 200 from collapsing, the reservoir 100 may be rigid in manner similar to the blood salvage system 100.

Figure 2:
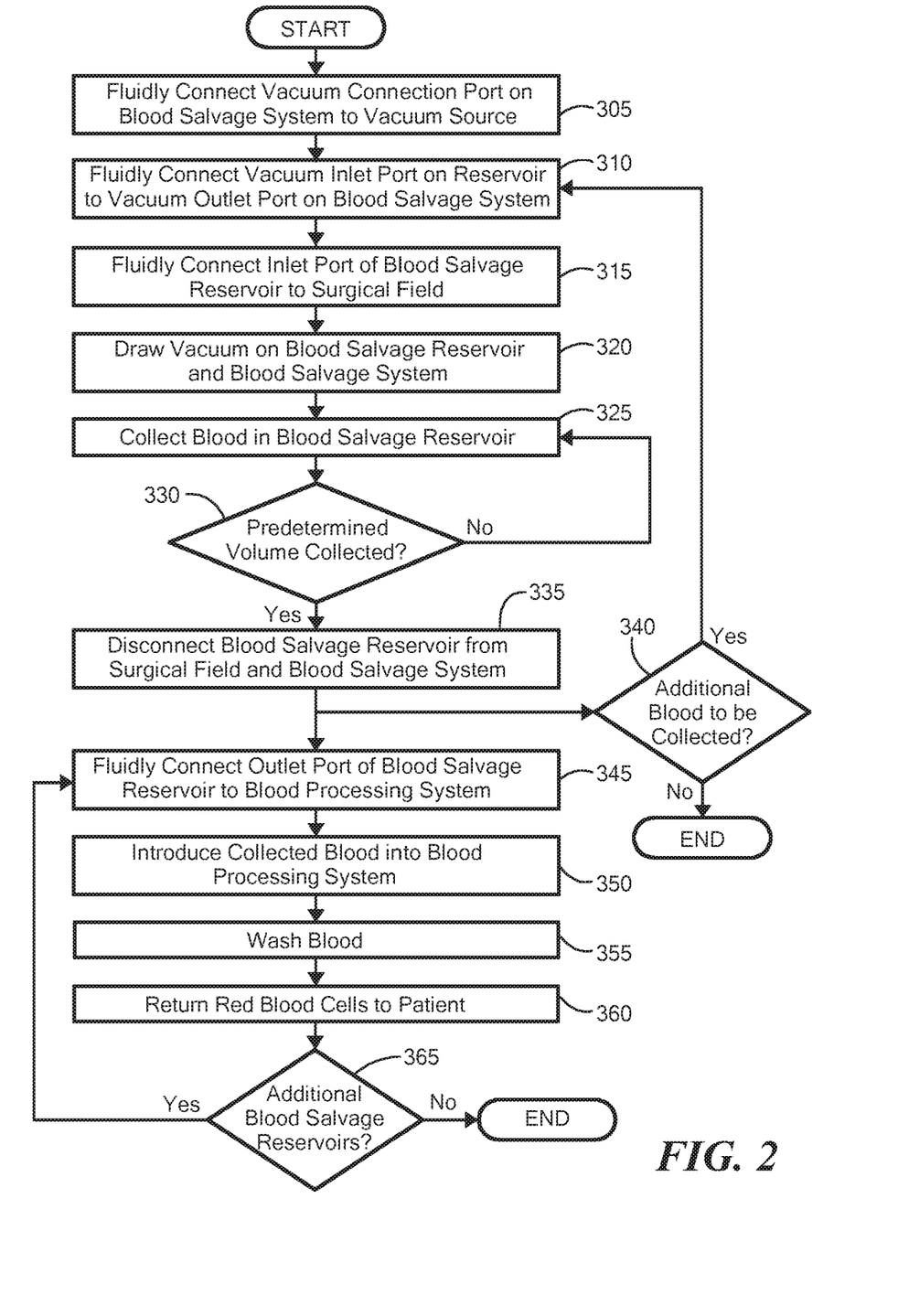
FIG. 2 is a flowchart depicting a method of collecting and washing shed blood, in accordance with various embodiments of the present invention.
Figure 3:
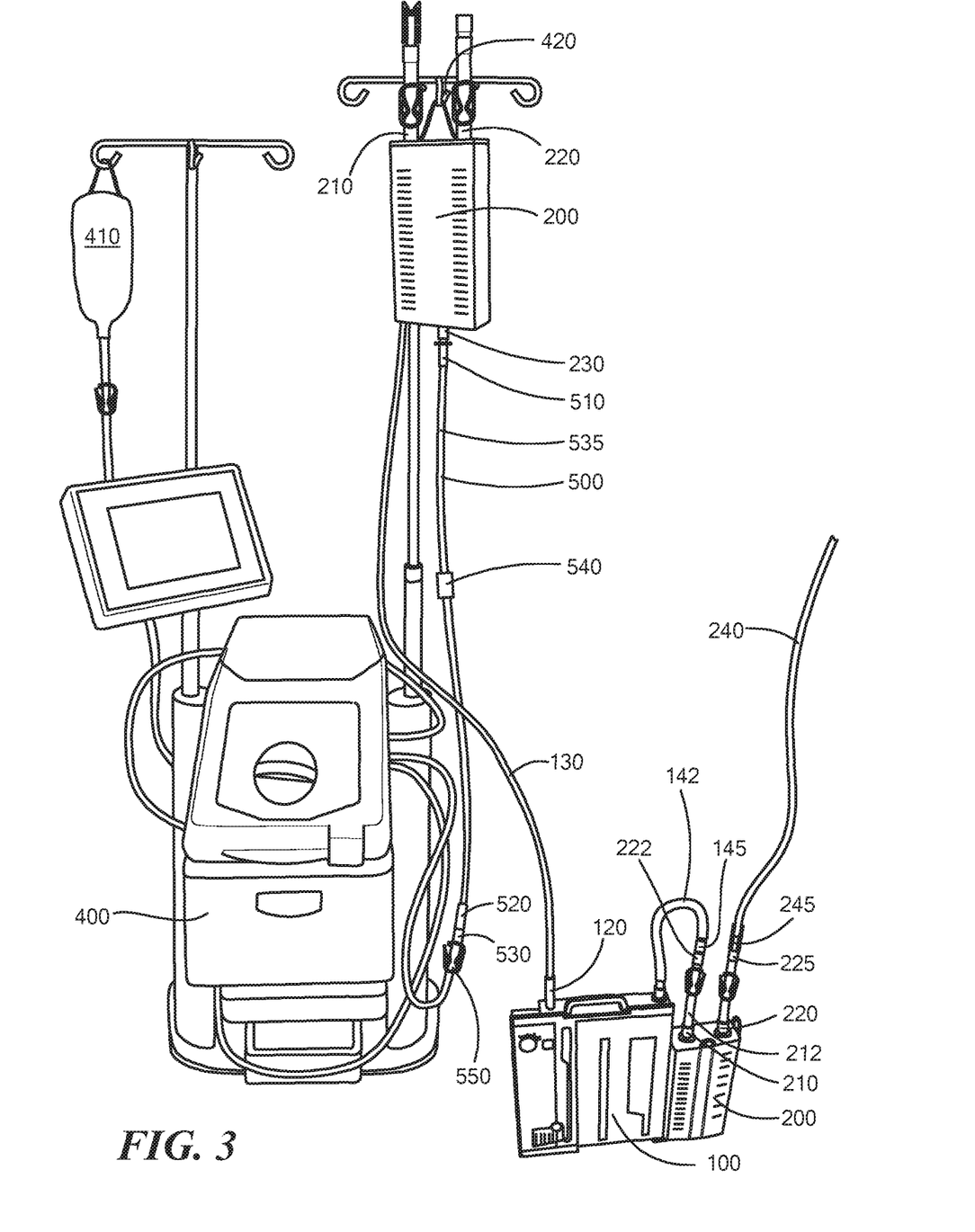
FIG. 3 schematically shows a blood salvage reservoir connected to a system for washing shed blood, in accordance with some embodiments of the present invention.

FIG. 2 is a flowchart depicting a method for collecting and washing shed blood in accordance with various embodiments of the present invention. FIGS. 3 and 4 schematically show the blood salvage system 100 and the blood salvage reservoir 200 at various stages of the collection and washing process. First, once the blood salvage system 100 and reservoir 200 are removed from any packaging, the user may fluidly connect the vacuum port 120 on the blood salvage system 200 to a vacuum source (not shown) (Step 305; FIG. 3). For example, the user may connect one end of the vacuum tube 130 to the vacuum port 120 and the other end to the vacuum source. Once the vacuum source is connected, if the blood salvage system 100 is equipped with the control regulator 150, the user can adjust the level of suction to the desired level.

In some embodiments, the blood salvage system 100 may come already connected to the blood salvage reservoir 200 (e.g., the vacuum outlet port 140 may be fluidly connected to the vacuum inlet port 210 on the reservoir 200). However, if the system 100 and reservoir 200 are not already connected, the user may fluidly connect the vacuum outlet port 140 on the blood salvage system 100 to the vacuum inlet port 210 on the reservoir 200 (e.g., by connecting the connector 145 on the vacuum outlet port 140 to the connector 215 on the vacuum inlet port 210) (Step 310; FIG. 3). Once this connection is made, the vacuum source and the blood salvage system 100 are ready to pull a vacuum on the reservoir 200.

In order to collect the blood from the surgical site (e.g., the shed blood), the user may then (e.g., using connectors 225 and 245) connect the inlet port 220 of the reservoir 200 to a patient tube 240 leading to the patient/surgical site (Step 315; FIG. 3). Once fully connected, if the vacuum source is not already on and pulling a vacuum, the user may turn on the vacuum to draw a vacuum on the reservoir 200 (Step 320) via the blood salvage system 100. This, in turn, will begin to draw the shed blood through the patient line 240 and into the blood salvage reservoir 200, where it is collected (Step 325; FIG. 3).

In many applications, a critical volume of shed blood is collected before the collected blood is further processed and/or returned to the patient. To that end, the user may monitor the volume of blood collected within the reservoir (Step 330). Alternatively, the system/method may utilize a scale or other measurement device to determine the volume of blood collected in the reservoir 200. Once a predetermined volume of blood is collected, the user will then have sufficient blood to process further.

It is important to note that the predetermined volume of blood can be dependent upon a number of factors including, but not limited to, the surgical application (e.g., cardiac surgery), the type of drain (e.g., a chest drain, an aspiration and anticoagulation line, etc.), whether the collection is conducted post-operatively or intra-operatively, the patient (e.g., whether the patient is an adult or child), the blood processing device to be used to wash the collected blood (e.g., the size of any blood component separation device used), etc. However, in some embodiments, the predetermined volume of blood may be between 100 mL and 500 mL (e.g., 250 mL). Alternatively, in other embodiments, the predetermined volume may be less than 100 mL (e.g., the predetermined volume may be 25 ml, 50 mL, 75 mL, etc.). In further embodiments, the predetermined volume may be greater than 500 mL (e.g., the predetermined volume may be 550 mL, 600 mL, 650 mL, 700 mL, etc.). Additionally or alternatively, if the blood processing system utilizes a blood component separation device (e.g., a centrifuge bowl), the predetermined volume may be equal to the twice the volume of that of the centrifuge bowl (e.g., if the bowl is 275 mL, the predetermined volume may be approximately 550 mL).

Once a sufficient volume of shed blood is collected within the reservoir 200 (e.g., the predetermined volume of shed blood), the user may close the patient line 140 (e.g., using a valve located on the patient line) to prevent spillage of the shed blood, and may disconnect the blood salvage reservoir 200 from the surgical field/patient line 140 and from the blood salvage system 100 (step 335). Once the reservoir 200 is disconnected, no additional shed blood is collected within the reservoir 200. However, if there is additional blood to be collected (e.g., if the surgery is still on going in intra-operative applications or the patient is still bleeding in post-operative applications) (Step 340), the user may connect a new blood salvage reservoir 200 to the patient and the blood salvage system 200. For example, like the first reservoir 200, the user may fluidly connect the vacuum outlet port 140 on the blood salvage system 100 to the vacuum inlet port 210 on the new reservoir 200 and connect the inlet port 220 on the new reservoir 200 to the patient line. The user may then open the patient line 240 (e.g., by opening the valve), and continue collecting shed blood within the new reservoir 200 (e.g., Steps 310 to 335 may be repeated for the new/second salvage reservoir 200).

To begin processing the collected blood, the user may, optionally, hang the reservoir 200 from a hook 420 located on the blood processing system 400, and then connect the outlet port 230 on the reservoir 200 to the blood processing system 400 (Step 345; FIGS. 3 and 4). As mentioned above, the outlet port 230 of the reservoir may be a spike port. To that end, the user may utilize a connection set 500 similar to that shown in FIG. 5. For example, the connection set 500 may include a spike 510 that can be inserted into the outlet port 230 on the reservoir 200, and a connector 520 that connects to a counterpart connector 530 on section of tubing 535 leading to the blood processing system 400. Therefore, to connect the reservoir 200 to the blood processing system 400, the user may connect the two connectors 520/530 and push the spike 510 into the outlet port 230.

Figure 5:
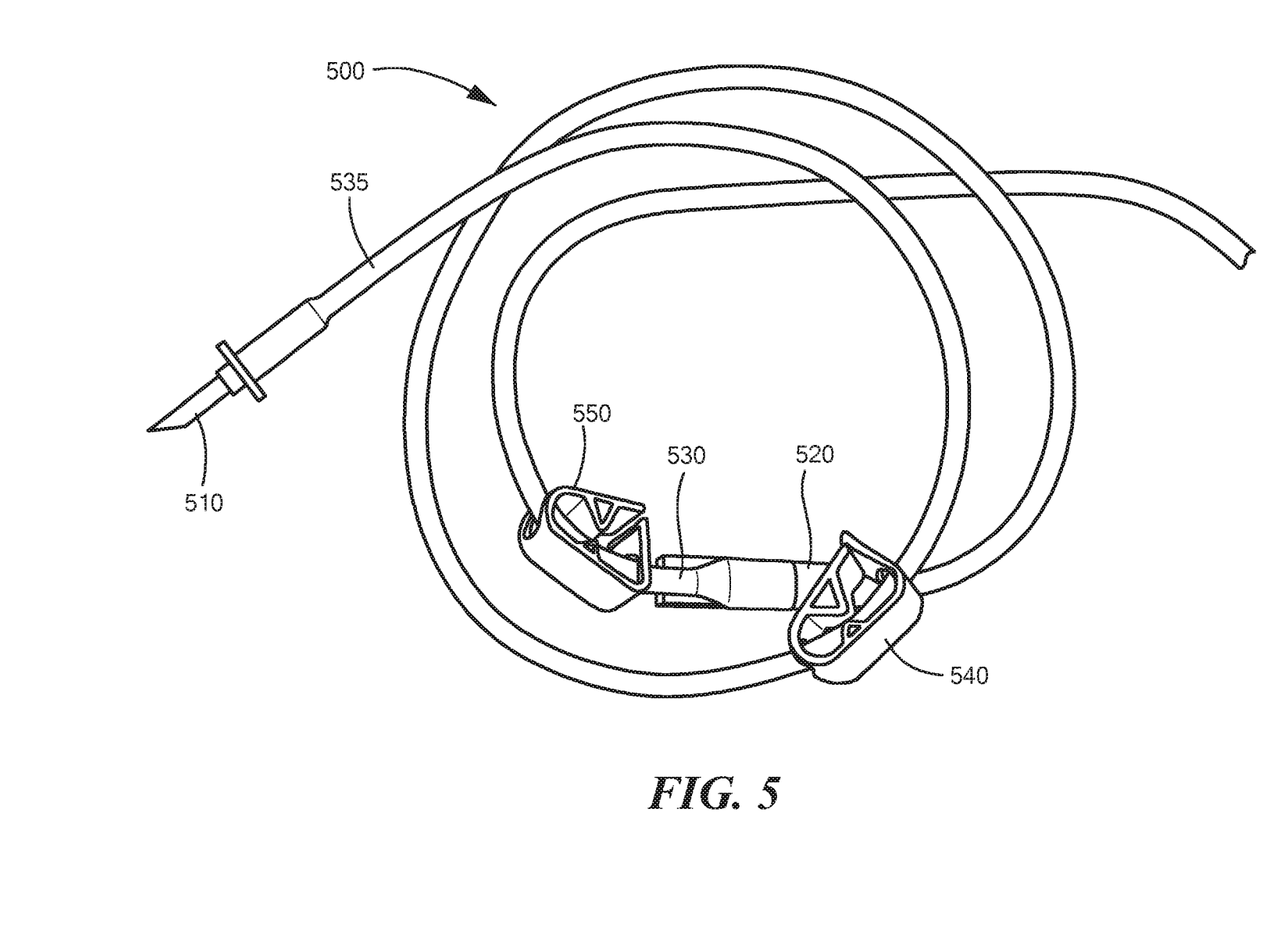
FIG. 5 schematically shows a connection set for connecting the blood salvage reservoir shown in FIG. 4 with the system for washing shed blood shown in FIG. 3, in accordance with some embodiments of the present invention.

When the reservoir 200 is fully connected to the blood processing system 400, the user may then begin introducing the collected blood into the blood processing system 400 (Step 350). To that end, to begin fluid flow from the reservoir 200, the user may open the valves 540/550 located on the connection set 500 and the tubing 535 leading to the blood processing system 400. The blood may then gravity feed into the blood processing system 400. Alternatively, in some embodiments, the blood processing system 400 may include a pump that draws the blood from the reservoir 200, through the collection set 500 and tube 535, and into the blood processing system 400. The blood processing system 400 will then wash the blood (Step 355) and return at least a portion of the washed blood (e.g., one or more of the components of the blood, for example, red blood cells) to the patient (Step 360). If the system has collected additional reservoirs of blood (Step 365), the user may then connect any additional reservoirs 200 to the blood processing system 400 and process/wash the blood in a similar manner.

It is important to note that a number of types for blood processing systems may be used to process and/or wash the collected blood. For example, various embodiments of the present invention may use commercial blood salvage and processing systems such as the OrthoPAT® Surgical Blood Salvage System, the CardioPAT™ Surgical Blood Salvage System, the Cell Saver® Blood Salvage System (e.g., the Cell Saver® Elite® and/or Cell Saver® 5+ systems), all of which are sold by Haemonetics Corporation of Braintree, Mass.

Some of the commercially available blood salvage and processing systems mentioned above (e.g., the Cell Saver® Elite® and/or Cell Saver® 5+ systems) include a blood component separation device (e.g., a centrifuge bowl) that separates the whole blood into its individual components. For example, in embodiments using such processing systems, anticoagulant may be added (from an anticoagulant bag 410 connected to the processing system 400; FIG. 3) to the collected shed blood as it is transferred to the processing system 400. The blood is then introduced into the blood component separation device, which separates the whole blood into its individual components (e.g., red blood cells, plasma, platelets, etc.). Once the blood is separated, the platelets and/or plasma may be transferred to a waste bag for disposal, and the processing system 400 may introduce a wash solution into the separation device to wash the red blood cells. After washing the red blood cells, the processing system 400 may return the red blood cells to the patient.

Although the embodiments described above utilize blood salvage reservoirs 200 that are flexible and include an outlet port 230 located on the bottom, other embodiments can utilize different reservoirs. For example, some embodiments may utilize a rigid reservoir. Additionally or alternatively, some embodiments may utilize reservoirs that do not include an outlet port 230 on the bottom. In such embodiments, the user may utilize the inlet port 220 to transfer the collected shed blood from the reservoir 200 to the blood processing system 400 by connecting the connection set 500 (in such embodiments a connector other than the spike 510 may be required to connect to the inlet port 220) to the inlet port 220 and inverting the reservoir 200 such that the blood will exit the reservoir 200 via the inlet port 220 and flow into the blood processing system 400.

Alternatively, some embodiments may not use a reservoir 200 at all. Rather, the shed blood may be collected directly into the blood salvage system 100 (e.g., the blood salvage system 100 may act as a collection reservoir). To that end, the vacuum outlet port 140 on the blood salvage system 100 may act as an inlet, and the patient line may be connected directly to the vacuum outlet port 140. Therefore, when a vacuum source is connected, the vacuum will draw the shed blood through the patient line and into the blood salvage system 100. Additionally, in such embodiments, to wash the collected blood, the patient line 240 may be disconnected from and the connection set 500 may be connected to the vacuum outlet port 140 (or the blood salvage system 100 may include an outlet port in a manner similar to the reservoir). Alternatively, in a manner similar to the blood salvage reservoir 200, the blood salvage system 100 may have a separate outlet port.

It should be noted that, although the method is described above as being performed in a specified order, in some embodiments, the order of the method steps can be rearranged. For example, the order of the connections (e.g., steps 305 to 315) can be rearranged such that the vacuum source is connected after the vacuum inlet port 210 is connected to the vacuum outlet port 140 or after the inlet port 220 is connected to the surgical field.

Figure 6:
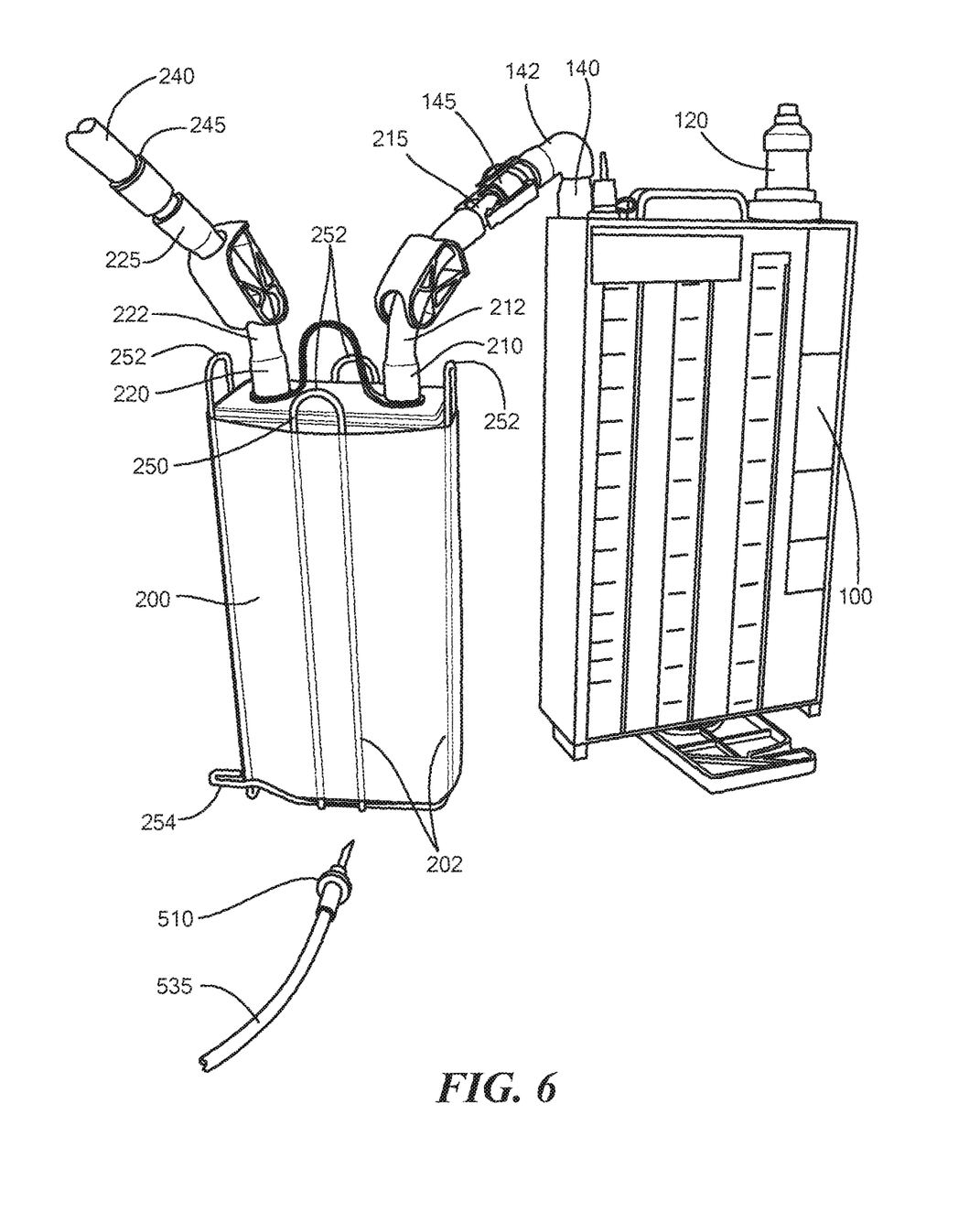
FIG. 6 schematically shows an alternative system for collecting shed blood, in accordance with further embodiments of the present invention.

It is important to note that, although the embodiment described above utilizes a Teleflex Pluer-Evac® A-9250-08LF blood salvage system, other blood salvage systems may be used. For example, as shown in FIG. 6, some embodiments of the present invention may utilize blood salvage systems produced by Covidien—in particular, the Altitude™ chest drainage unit.

The embodiments of the invention described above are intended to be merely exemplary; numerous variations and modifications will be apparent to those skilled in the art. All such variations and modifications are intended to be within the scope of the present invention as defined in any appended claims.

What is claimed is:

1. A method for collecting and washing shed blood comprising:
    providing a first blood salvage reservoir having an inlet port, an outlet port and a vacuum inlet port;
    providing a blood salvage system having a vacuum connection port and a vacuum outlet port, the vacuum inlet port on the first blood salvage reservoir fluidly connected to the vacuum outlet port on the blood salvage system;
    fluidly connecting the inlet port of the first blood salvage reservoir to a surgical field of a patient, the inlet port configured to allow blood lost during a surgical procedure to be collected within the first blood salvage reservoir;
    fluidly connecting the vacuum connection port on the blood salvage system to a vacuum source;
    drawing a vacuum on the first blood salvage reservoir and the blood salvage system to draw blood from the surgical field and into the blood salvage reservoir;
    collecting a volume of shed blood within the first blood salvage reservoir;
    disconnecting the first blood salvage reservoir from the surgical field and from the blood salvage system;
    fluidly connecting a second blood salvage reservoir to the surgical field and blood salvage system to continue drawing blood from the surgical field;
    fluidly connecting the outlet port of the first blood salvage reservoir to an automated blood processing system;
    introducing the collected blood into the automated blood processing system;
    washing, using the automated blood processing system, the blood introduced into the automated blood processing system; and
    returning at least a portion of the washed blood to the patient.

2. A method according to claim 1, wherein the at least a portion of the washed blood is returned autologously.

3. A method according to claim 1, wherein washing the blood introduced into the automated blood processing system includes:
    introducing anticoagulant into the collected blood;
    introducing the anticoagulated blood into a blood component separation device, the blood component separation device separating the anticoagulated blood into red blood cells and at least a second blood component;
    sending the at least a second blood component to a waste container; and
    introducing a wash solution into blood component separation device to wash the red blood cells.

4. A method according to claim 3, wherein returning at least a portion of the washed blood to the patient includes returning the washed red blood cells to the patient.

5. A method according to claim 1, wherein the first blood salvage reservoir is a flexible reservoir.

6. A method according to claim 1, wherein the blood salvage system includes a rigid housing.

7. A method according to claim 1, further comprising monitoring an amount of blood collected within the first blood salvage reservoir.

8. A method according to claim 7, wherein disconnecting the first blood salvage reservoir from the surgical field and from the blood salvage system includes disconnecting the first blood salvage reservoir when a predetermined volume of blood is collected within the first blood salvage reservoir.

9. A method according to claim 8, wherein the predetermined volume blood is between 100 mL and 500 mL.

10. A method according to claim 1, wherein connecting the first blood salvage reservoir to the surgical site includes connecting the first blood salvage reservoir to a chest drain.

11. A method according to claim 1, wherein the first blood salvage reservoir is connected to the surgical site via a patient line.

12. A method according to claim 1, wherein the surgical site is an intra-operative surgical site and connecting the first blood salvage reservoir to the surgical site includes connecting the first blood salvage reservoir to an aspiration and anticoagulant line.

13. A method according to claim 1, wherein the outlet port of the first blood salvage reservoir is fluidly connected the automated blood processing system via a fluid connection set.

14. A method according to claim 13, wherein the fluid connection set includes:
    a first connector configured to connect to the outlet port of the first blood salvage reservoir;
    a second connector configured to connect to an inlet on the automated blood processing system; and
    a tube extending between the first and second connector and configured to fluidly connect the first blood salvage reservoir and the automated blood processing system.

15. A method according to claim 14, wherein the first connector is a spike.

16. A method according to claim 14, wherein the fluid connection set includes at least one valve located on the tube and configured to prevent the flow of fluid through the tube.

17. A method according to claim 1, wherein the first blood salvage reservoir is contained within a rigid frame that is configured to support the first blood salvage reservoir.

18. A method according to claim 1, wherein disconnecting the first blood salvage reservoir from the surgical field and from the blood salvage system includes:

fluidly disconnecting the inlet port on the first blood salvage reservoir from the surgical field; and fluidly disconnecting the vacuum inlet port on the first blood salvage reservoir from the vacuum outlet port on the blood salvage system.

19. A method according to claim 1, wherein fluidly connecting the second blood salvage reservoir to the surgical field and the blood salvage system includes:

fluidly connecting a vacuum inlet port on the second blood salvage reservoir to the vacuum outlet port on the blood salvage system; and fluidly connecting an inlet port on the second blood salvage reservoir to the surgical field of the patient.

20. A method for collecting and washing shed blood comprising:

providing a first blood salvage reservoir having an inlet port, an outlet port and a vacuum inlet port;

providing a blood salvage system having a vacuum connection port and a vacuum outlet port;

fluidly connecting the vacuum inlet port on the first blood salvage reservoir to the vacuum outlet port on the blood salvage system;

fluidly connecting the inlet port of the first blood salvage reservoir to a surgical field of a patient, the inlet port configured to allow blood lost during a surgical procedure to be collected within the first blood salvage reservoir;

fluidly connecting the vacuum connection port on the blood salvage system to a vacuum source;

drawing a vacuum on the first blood salvage reservoir and the blood salvage system to draw blood from the surgical field and into the blood salvage reservoir;

collecting a volume of shed blood within the first blood salvage reservoir;

disconnecting the first blood salvage reservoir from the surgical field and from the blood salvage system;

fluidly connecting a second blood salvage reservoir to the surgical field and blood salvage system to continue drawing blood from the surgical field;

fluidly connecting the outlet port of the first blood salvage reservoir to an automated blood processing system;

introducing the collected blood into the automated blood processing system;

washing, using the automated blood processing system, the blood introduced into the automated blood processing system; and returning at least a portion of the washed blood to the patient.

21. A method of blood salvage collection, processing and autologous reinfusion comprising:

providing a first blood salvage reservoir having an inlet port and at least one outlet port and connecting the inlet port to the surgical field of a patient to collect blood lost during a surgical procedure;

providing a rigid reservoir having an inlet and outlet and connecting the inlet to the outlet of the first blood salvage reservoir and connecting the outlet to a source of suction;

operating the source of suction to draw blood from the surgical field into the first blood salvage reservoir;

disconnecting the first blood salvage reservoir from the surgical field and from the rigid reservoir;

connecting a second blood salvage reservoir to the surgical field and rigid reservoir to continue suctioning blood from the surgical field;

connecting an outlet of the first blood salvage reservoir to a fluid pathway inlet of an automated blood processing system; and operating the automated blood processing system to clean the salvaged blood and return it autologously to the patient.

22. A system for collecting and washing shed blood comprising a first blood salvage reservoir for collecting shed blood, the first blood salvage reservoir including:
a flexible housing defining the first blood salvage reservoir,
an inlet port configured to be fluidly connected to a surgical field of a patient, such that shed blood may be collected within the flexible housing,
a vacuum inlet port configured to allow a vacuum to be drawn on the first blood salvage reservoir to draw fluid from the surgical site and into the first blood salvage reservoir, and
an outlet located on a bottom surface of the flexible housing;

a blood salvage system including:
a rigid housing defining the blood salvage system,
a vacuum connection port configured to be fluidly connected to a vacuum source, and
a vacuum outlet port configured to be fluidly connected the vacuum inlet port on the first blood salvage reservoir, thereby allowing a vacuum to be drawn on the first blood salvage reservoir; and a fluid connection set including:
a first connector configured to connect to the outlet port on the first blood salvage reservoir,
a second connector configured to connect to an inlet on an automated blood processing system, and
a tube extending between the first and second connectors, the fluid connection set configured to fluidly connect the outlet of the first blood salvage reservoir and the automated blood processing system, the first blood salvage reservoir having a collection mode in which the inlet port is fluidly connected to the surgical site and the vacuum inlet port is fluidly connected to the vacuum outlet port on the blood salvage system, the first blood salvage reservoir configured to collect shed blood from the surgical site when in the collection mode, the first blood salvage reservoir also having a processing mode in which the inlet port is fluidly disconnected from the surgical site, the vacuum inlet port is fluidly disconnected from the vacuum outlet port on the blood salvage system, and the first connector on the fluid connection set is connected to the outlet, thereby fluidly connecting the first blood salvage reservoir to the automated blood processing system, the automated blood processing system configured to process and autologously reinfuse at least a portion of the shed blood.

23. A system according to claim 22, further comprising a second blood salvage reservoir for collecting shed blood, the second blood salvage reservoir including:

a second flexible housing defining the second blood salvage reservoir, a second inlet port configured to be fluidly connected to the surgical field when the first blood salvage reservoir is in the processing mode, such that shed blood may be collected within the second flexible housing, and a second vacuum inlet port configured to allow a vacuum to be drawn on the second blood salvage reservoir to draw fluid from the surgical site and into the second blood salvage reservoir when the first blood salvage reservoir is in the processing mode.

* * * * *

UNITED STATES PATENT AND TRADEMARK OFFICE
CERTIFICATE OF CORRECTION

PATENT NO. : 10,500,330 B2  
APPLICATION NO. : 15/517351  
DATED : December 10, 2019  
INVENTOR(S) : Donald J. Schwarz et al.

It is certified that error appears in the above-identified patent and that said Letters Patent is hereby corrected as shown below:

In the Claims

Column 12, Claim 22, Line 7, after the word comprising, the ":" is missing.

Signed and Sealed this
Twenty-eighth Day of April, 2020

Andrei Iancu
*Director of the United States Patent and Trademark Office*